United States Patent
Bhunachet

(10) Patent No.: US 7,330,749 B1
(45) Date of Patent: Feb. 12, 2008

(54) FLUORESCENCE ELECTRONIC ENDOSCOPIC SYSTEM

(76) Inventor: Ekapot Bhunachet, 2-32-22 Kasuga, Tsukuba, Ibaraki (JP) 305-0821

( * ) Notice: Subject to any disclaimer, the term of this patent is extended or adjusted under 35 U.S.C. 154(b) by 0 days.

(21) Appl. No.: 09/936,872

(22) PCT Filed: Mar. 15, 2000

(86) PCT No.: PCT/JP00/01558

§ 371 (c)(1), (2), (4) Date: Sep. 17, 2001

(87) PCT Pub. No.: WO00/54652

PCT Pub. Date: Sep. 21, 2000

(30) Foreign Application Priority Data

Mar. 17, 1999 (JP) ................. 11-114022

(51) Int. Cl.
*A61B 6/00* (2006.01)
(52) U.S. Cl. .............. 600/476; 600/109; 600/473; 600/478
(58) Field of Classification Search .......... 600/473, 600/475, 476, 477, 478, 407, 425, 178, 180, 600/181, 118, 109, 160, 310, 474; 356/435, 356/445, 448
See application file for complete search history.

(56) References Cited

U.S. PATENT DOCUMENTS

| | | | |
|---|---|---|---|
| 4,535,758 A * | 8/1985 | Longacre, Jr. ............. 600/109 |
| 5,590,660 A * | 1/1997 | MacAulay et al. ......... 600/478 |
| 5,827,190 A * | 10/1998 | Palcic et al. ............... 600/476 |
| 5,891,016 A | 4/1999 | Utsui et al. |
| 6,099,466 A | 8/2000 | Sano et al. |
| 6,148,227 A * | 11/2000 | Wagnieres et al. ......... 600/476 |
| 6,280,378 B1 | 8/2001 | Kazuhiro et al. |
| 6,471,636 B1 | 10/2002 | Sano et al. |
| 6,665,556 B1 * | 12/2003 | Alfano et al. .............. 600/473 |

FOREIGN PATENT DOCUMENTS

JP 63-122421 A 6/1988

(Continued)

OTHER PUBLICATIONS

Sutedja TG, Vermans BJ, Smit EF, Postmus PE. Fluorescence bronchoscopy for early detection of lung cancer: A clinical perspective. Lung Cancer 2001, 34: 157-168.

(Continued)

*Primary Examiner*—Brian L. Casler
*Assistant Examiner*—Michael Rozanski

(57) ABSTRACT

In fluorescent endoscopic examinations, excitation light and light adjusted by an adjuster filter are alternately projected to an object under observation, the fluorescence light is received by one channel out of three channels by disposing barrier filters before a black-and-white CCD, or received without any filter by the channel of a color CCD which does not react with excitation light but with the fluorescent light, the light adjusted by an adjuster filter is received by the other two channels to capture the background image, the signals sent through the three channels are combined, and the fluorescent image is superimposed on the background image on a monitor. Thus, a sharp fluorescent image and bright field of view are formed and viewed on the same screen simultaneously, and the portions where fluorescence is emitted can be easily specified in the background.

7 Claims, 3 Drawing Sheets

FOREIGN PATENT DOCUMENTS

| | | |
|---|---|---|
| JP | 2-299633 A | 12/1990 |
| JP | 3-97439 A | 4/1991 |
| JP | 3-97441 A | 4/1991 |
| JP | 3-97442 A | 4/1991 |
| JP | 4-92306 A | 3/1992 |
| JP | 6-125911 A | 5/1994 |
| JP | 8-140928 A | 6/1996 |
| JP | 9-70384 A | 3/1997 |
| JP | 9-154812 A | 6/1997 |
| JP | 9-327433 A | 12/1997 |
| JP | 10-500588 A | 1/1998 |
| JP | 10-295633 A | 11/1998 |

OTHER PUBLICATIONS

Lam S, MacAulay C, Hung J, et al. Detection of dysplasia and carcinoma in situ with a lung imaging fluorescence endoscope device. J Thorac Cardiovasc Surg. 1993; 105: 1035-1040.

Lam S, Kennedy T, Unger M, et al. Localization of bronchial intraepithelial neoplastic lesions by fluorescence bronchoscopy. Chest. 1998; 118: 696-702.

Nakaniwa N, Namishima A, Ogihara T, et al. Newly developed autofluorescence imaging videoscope system for the detection of colonic neoplasms. Digestive Endoscopy 2005; 17: 235-240.

Uedo N, Iishi H, Tatsuta M, et al. A novel videoendoscopy system by using autofluorescence and reflectance imaging for diagnosis of esophagogastric cancers. Gastrointestinal Endoscopy 2005; 62: 521-528.

Kara MA, Peters FP, Kate FJWT, et al. Endoscopic video autofluorescence imaging may improve the detection of early neoplasia in patients with Barrett's esophagus. Gastrointestinal Endoscopy 2005; 61: 679-685.

Chiyo M, Shibuya K, Hoshino H, et al. Effective detection of bronchial preinvasive lesions by a new autofluorescence imaging bronchovideoscope system. Lung Cancer 2005; 48: 307-313.

Leonhard M. New incoherent autofluorescence/fluorescence system for early lung cancer Diagn Ther Endosc 1999; 5: 71-75.

Herth FJF, Ernst A, Becker HD. Autofluorescence bronchoscopy—a comparison of two systems (LIFE and D-light). Respiration 2003; 70: 395-398.

Adachi R, Utsui T, Furusawa K. Development of the autofluorescence endoscope imaging system. Diagn Ther Endosc 1999; 5: 65-70.

Kakihana M, H KK, Okunaka T, et al. Early detection of bronchial lesions using system of autofluorescence endoscopy (SAFE) 1000. Diagn Ther Endosc 1999; 5: 99-104.

Olympus News Release: Evis Lucera Spectrum is launched, endoscopic video imaging system for observation using specific light spectra. May 16, 2006. (available at: http://www.olympus-global.com/en/news/2006a/nr060515evise.cfm Accessed Sep. 4, 2007).

Olympus News Release: World's First Gastrointestinal Videoscopes with Auto Fluorescence Imaging Capability. Jan. 17, 2007. (available at: http://www.olympus-global.com/en/news/2007a/nr070117evise.cfm Accessed Sep. 4, 2007).

Baillie J. The endoscope. Gastrointestinal Endoscopy, 2007; 65: 886-893.

Tada M, Shimizu S, Iso A, et al. Computer analysis of electronic colonscopic image after administration of fluorescent material. Gastroenterol Endosc 1993; 35: 483-488.

Bhunchet E, Hatakawa H, Sakai Y, et al. Fluorescein electronic endoscopy: a novel method for detection of early stage gastric cancer not evident to routine endoscopy. Gastrointestinal Endoscopy 2002; 55: 562-571.

Bergman JJGH. Diagnosis and therapy of early neoplasia in Barrett's esophagus. From current opinion in Gastroenterology (available at: http://www.medscape.com/viewarticle/506569_ Accessed Aug. 17, 2007).

Ikeda N, Honda H, Hayashi A, et al. Early detection of bronchial lesions using newly developed videoscopy-based autofluorescence bronchoscopy. Lung Cancer 2006; 52: 21-27.

Nakaniwa N, Namishima A, Ogihara T, Ohkawa A, Abe S, Nagahara A, et al. Newly-developed autofluorescence imaging videoscope system for the detection of colonic neoplasms, Digestive Endoscopy 2005; 17: 235-240.

Chiyo M, Shibata K, Hoshino H, Yasufuku K, Sakine Y, Lizasa T, et al. Effective detection of bronchial preinvasive lesions by a new autofluorescence imaging bronchovideoscope system. Lung Cancer 2005;48:307-313.

Kara MA, Peters FP, tan Kate FJW, van Deventer SJ, Fockens P, Bergman JJGHM. Endoscopic video autofluorescence imaging may improve the detection of early neoplasia in patients with Barrett's esophagus. Gastrointestinal Endoscopy 2005;51:679-685.

Bhunchet E, Hatakawa H, Sakai Y, Shibata T. Fluorescein electronic endoscopy: a novel method for detection of early stage gastric cancer not evident to routine endoscopy. Gastrointestinal Endoscopy 2002;55:562-571.

* cited by examiner

FLUORESCENCE ELECTRONIC ENDOSCOPIC SYSTEM

CROSS-REFERENCE TO RELATED APPLICATIONS

International application No. PCT/JP00/01558
International filing date Mar. 15, 2000
Priority date Mar. 17, 1999

STATEMENT REGARDING FEDERALLY SPONSORED RESEARCH OR DEVELOPMENT

Not applicable

REFERENCE TO A MICROFICHE APPENDIX

Not applicable

BACKGROUND OF THE INVENTION

Recently fluorescence endoscopies such as light-induced fluorescence endoscopy and photodiagnosis have been developed in order to detect lesions occult to routine white light endoscopy. These fluorescence endoscopies are performed with the combination of fiberscope and high-sensitive fluorescence camera, and are thus clumsy to operate and their price is very expensive. Moreover, their fluorescent images are quite dim.

Fluorescein sodium is a fluorescent substance daily used in ophthalmology to reveal fine vascular structures of the retina. In the method of this fluorescein fundus photography, the exciter filter is used to select excitation light from light source and the barrier filter cuts all excitation light reflecting from the fundus but passes through all fluorescent light emitted. In order to a get sharp image, a multiple-layered interference exciter filter which strictly selects only excitation blue light with the most potency to excite fluorescein sodium is recommended.

During a short period of 1975-1976, using a fiberscope, Katsu et al succeeded in observing and recording fluorescence of fluorescein sodium on the stomach surface and noted that this fluorescence endoscopy could determine the extent of gastric cancer in the mucosa. However, this fluorescence fiber endoscopy had never been performed since then. According to Katsu, the reasons were as follows.

Firstly, fluorescein fiber-endoscopy had some problems in recording the findings. The images were so dim that it was necessary to force-develop (4 to 8 times) high sensitive films (ASA 160) used. The exciter filter used by Katsu et al. was fluorescein isothiocyanate (FITC) interference filter which selectively passes only the excitation blue light with a peak at 495 nm.

Secondly, that electronic endoscopy, which allows a physician to confirm findings at the time of examination, became popular was another reason that fluorescein fiber-endoscopy disappeared. This is because the FITC interference filter, which was recommended as exciter filter, did not function with an electronic endoscope. It gave even dimmer images being used with an electronic endoscope than used with a fiberscope. The way to solve this problem was thought to be using a more powerful light source but this has never succeeded. An FITC interference filter cannot stand the heat of the electronic endoscopic light source.

Thirdly, using a fiberscope, one can easily insert the barrier filter in front of the camera and take it away outside the body. But, using an electronic endoscope, the barrier filter has to be placed in front of the CCD located in the tip of the scope and it is very difficult to insert and remove the barrier filter while the electronic endoscope is inside the body. In order to do both routine and fluorescence electronic endoscopies, the scopes with and without the barrier filter have to be inserted into the body two times. This means two times of pain for the patient.

In 1993, Tada et al. analysed the change of electronic colonoscopic images after administration of fluorescein sodium by computer. In this study, electronic endoscopic images were sequentially recorded as digital data and processed by computer to accentuate the change with fluorescence. In other words, they did not succeed in observing the real time fluorescent images by electronic endoscopy.

BRIEF DESCRIPTION OF THE INVENTION

Recently, using a wide-banded light-balancing (LB) blue filter instead of a narrow-banded FITC interference filter, I succeeded in developing a new fluorescence electronic endoscopic system (FEES) able to perform fluorescence endoscopy by fluorescein sodium, i.e. fluorescein electronic endoscopy. With our FEES, real time changes of fluorescence can be clearly observed on a bright background image; thus, it is possible to perform biopsy and to photograph or video color print under a common condition. Compared to routine endoscopies, fluorescein electronic endoscopy can reveal more clearly and precisely the extents in the mucosa of early gastric cancer. I have declared how useful fluorescein electronic endoscopy is in detecting small gastric cancers occulted to white light endoscopy: at a cancer congress of Ibaraki prefecture on Feb. 21, 1997; at a Japanese cancer congress on Sep. 30, 1998; and at a Japanese digestive tract endoscopic congress on Nov. 19, 1998. Note that only the usefulness of fluorescein electronic endoscopy was discussed; but nothing concerning the content of the present invention has been announced.

In my FEES, excitation light (for example, blue light) and light adjusted by an adjuster filter are alternately projected to an object under observation. The fluorescence light (for example, yellow light) is received by a channel (for example, a blue channel) out of three channels by disposing before a black-and-white CCD a barrier filter which cuts all excitation light but passes all other light. The light adjusted by an adjuster filter is received by the other two channels (for example, a green and a red channel) to capture the background image. The signals sent through the three channels are combined, and the fluorescent image is superimposed on the background image on a monitor. Thus, a sharp fluorescent image and a bright field of view are formed and viewed on the same screen simultaneously, and the portions where fluorescence is emitted can be easily specified in the background.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

DETAILED DESCRIPTION OF THE INVENTION

The mechanism of FEES will be explained by the following experiment.

Experiment I

Mechanism of FEES

Figure 1:
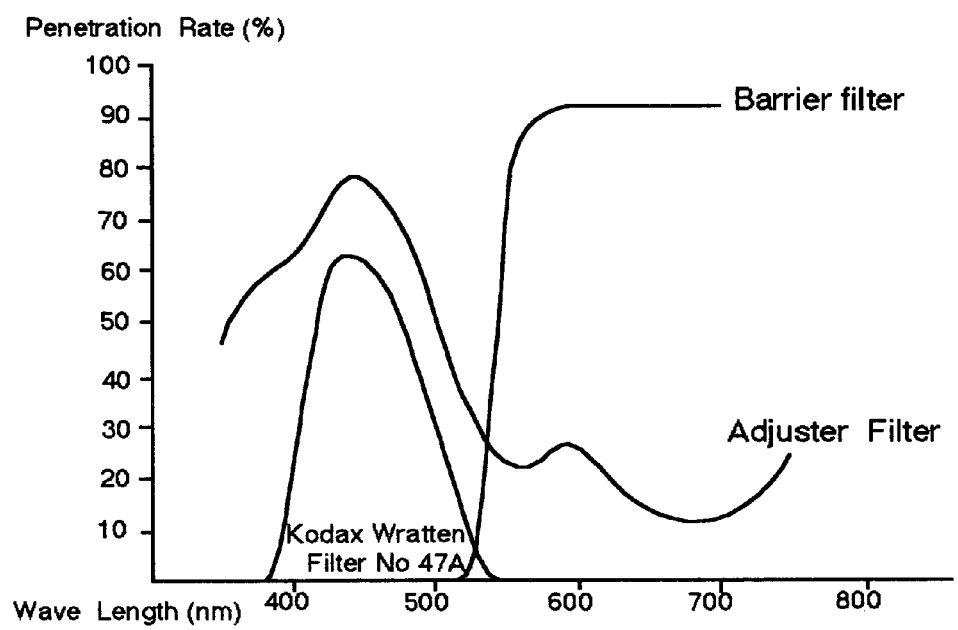
FIG. 1. The spectrograms of the barrier, adjuster and exciter filters used in experiments I and II is shown.

Diluted fluorescein sodium patched on white paper was observed with either/neither exciter filter (Kodak Wratten Filter No 47A, a recommended filter for activating fluorescein) or/nor adjuster filter (LB (light balancing) 200, Olympus) in front of light source by an electronic endoscope (Olympus, GIF, XQ200) with a barrier filter (Kodak Wratten Filter No 15) attached to the objective lens. The light source and video center system used were Olympus, CLV-U20D, and Olympus, CV-200 respectively. The spectrograms of the barrier, adjuster and exciter filters used are shown in FIG. 1.

Result

Experiment I

Mechanism of FEES

Figure 3:
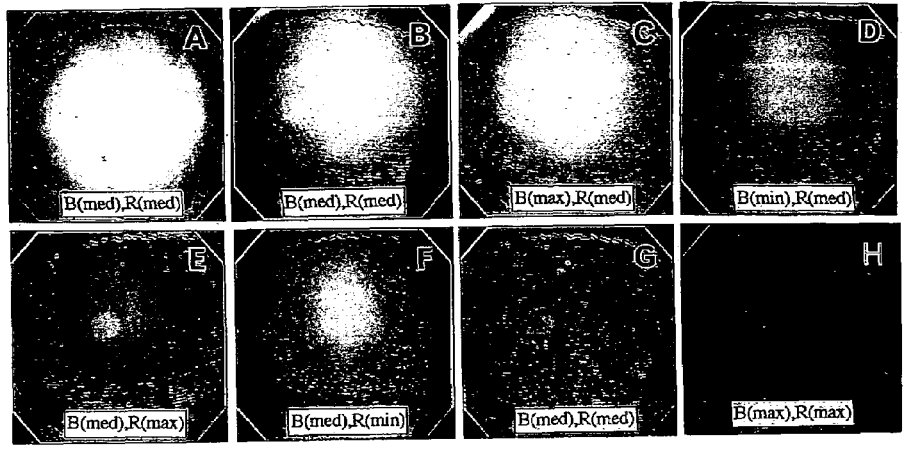
FIG. 3. Photographs show appearances of fluorescein stains on a white paper observed by an electronic endoscope (Olympus, GIF, XQ200) under different conditions. A: white light routine observation. B-F: with only a barrier filter attached to the objective lens. G: with an adjuster filter in front of the light source and the barrier filter. H: with an exciter filter in front of the light source and the barrier filter. B(max), B(med), B(min): strength of the blue channel of the monitor; maximum, medium and minimum, respectively. R(max), R(med), R(min): strength of the red channel of the monitor.

When commonly observed without a barrier filter, the stains of fluorescein sodium on white paper appeared yellowish, un-fluorescing (FIG. 3A). But, with only a barrier filter attached on the objective lens, fluorescein stains shined white fluorescence which became strongest when maximized and almost faded when the electronic signal of the blue channel was minimized. White paper appeared yellow (FIGS. 3 B, C and D). Strengthening the red channel made white paper look orange (FIG. 3E). On the other hand, weakening the red channel made white paper look green (FIG. 3F). However, strengthening and weakening the red channel did not influence the strength of white fluorescence arising on fluorescein stains (FIGS. 3E and F). With an adjuster filter in front of the light source and a barrier filter on the objective lens, white fluorescence of the fluorescein stain became stronger and its contour was clearer (FIG. 3G). White paper looked yellow but dimmer compared to with using a barrier filter only (FIG. 3G). With an exciter filter and a barrier filter, fluorescence of fluorescein stains looked blueish with sharp outlines. White paper became dark blue and its contour could not be observed (FIG. 3H).

Discussions

Figure 4:
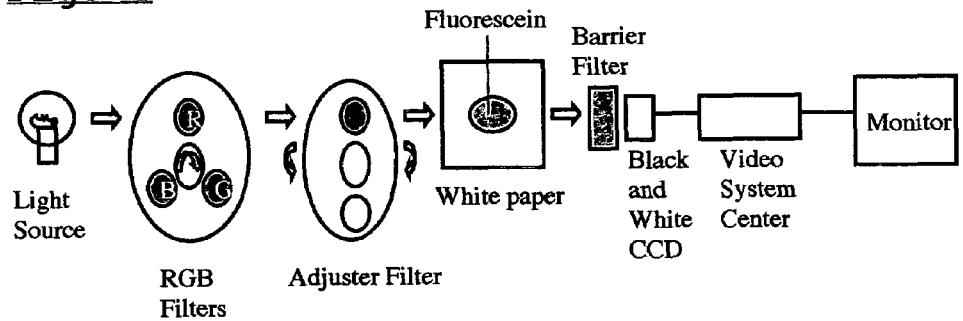
FIG. 4. Schema illustrate a fluorescence electronic endoscopic system able to perform fluorescence endoscopy by fluorescein sodium, in which a fluorescent image is received by one channel out of three channels by disposing before a black-and-white CCD a barrier filter.
Figure 5:
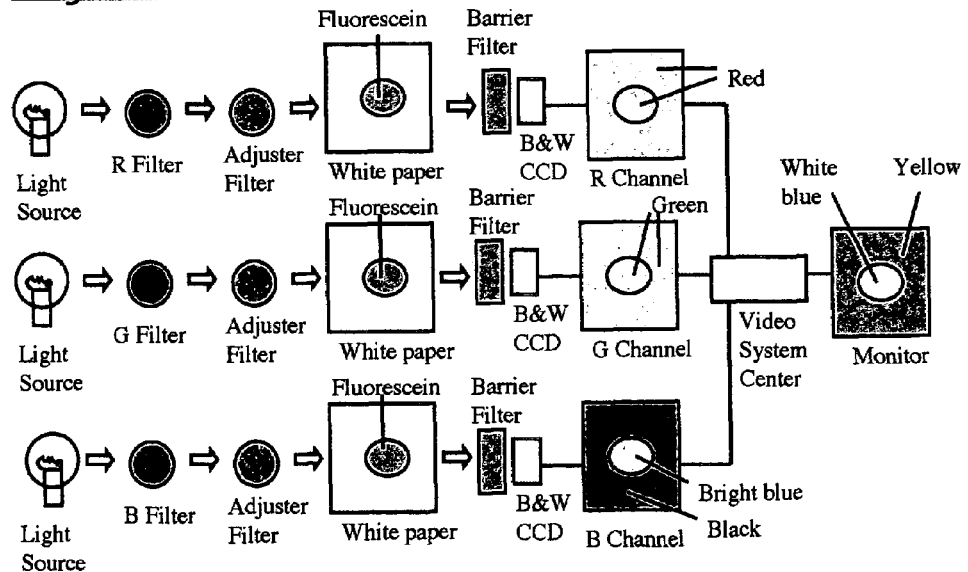
FIG. 5. Schema illustrate the mechanism of a fluorescence electronic endoscopic system able to perform fluorescence endoscopy by fluorescein sodium, in which a fluorescent image is received by one channel out of three channels by disposing before a black-and-white CCD a barrier filter.

In order to understand the mechanism of FEES, one has to know how the light source (Olympus, CLV-U20D), the electronic endoscope (Olympus, GIF, XQ200) and the video center system (Olympus, CV-200) used in this study function. In the light source, an RGB band pass filter is set in front of the lamp and is rotated to create in order three primary color lights, i.e., red, green and blue. A black and white CCD behind the objective lens of the endoscope picks up these three primary colors reflecting from observed materials and changes them to electronic signals as red (R), green (G) and blue (B) channel, respectively. The video center system receives these three channels of electronic signals and reconstructs them on a color TV monitor (FIG. 4).

When observed with only a barrier filter attached on the objective lens of an electronic endoscope with neither an exciter nor an adjuster filter, fluorescein stains appeared to shine white fluorescence and white paper appeared yellow on the TV monitor (FIG. 3B). This can be explained as follows: the primary blue light from the light source activates fluorescein sodium to yield a yellow fluorescence and meanwhile reflects almost completely from white paper; yellow fluorescence can totally pass through the barrier filter while blue light is completely shut off; the black and white CCD behind the barrier filter receives only yellow fluorescence from the fluorescein stain and transfers it to an electronic signal of the B channel. Therefore, when one looks on the B channel on the monitor, fluorescein stains appear bright blue and white paper appears dark blue. In the G and R phase, reflected primary green and red light from fluorescein stains and white paper are not so different in strength and the barrier filter does not cut green and red light, thus on the G and R channels both fluorescein stains and white paper appear bright. To confirm these findings, one can see each B, G and R channel by disconnecting the other 2 channels from the monitor. Reconstructing the R, G and B channels on the monitor results in the image of white stains (bright blue+green+red) and yellow paper (dark blue+green+red) (FIG. 3). From the explanation above, it is easy to understand why the white fluorescence of fluorescein stains looked strongest when maximized (FIG. 3C) and faded away when the electronic signals of B channel were minimized (FIG. 3D).

The adjuster filter used in this study passes lot of blue light and a part of green and red light (FIG. 1). When set in front of a light source, it helps by concentrating blue light at blue phase and cuts off to some extent green and red light at green and red phase. That is why, with the combination of an adjuster and a barrier filter, fluorescein stains shone stronger fluorescence and their outlines were emphasized while background, i.e. white paper, still appeared yellow but dimmer than without an adjuster filter (FIG. 3G).

The exciter filter passes selectively blue light but neither green nor red light (FIG. 1). Thus, with this filter and barrier filter, at B phase fluorescein stains became most bright blue and white paper became dark; however, at G and R phase both fluorescein stains and white paper became dark because primary green and red light were completely cut off. Reconstruction of the three channels results only in bright blue stains on a dark background (FIG. 3H). Compared with the combination of an adjuster and a barrier filter, fluorescence obtained from the combination of an exciter and a barrier filter is much dimmer.

Experiment II

Fluorescence Electronic Endoscopy by Fluorescein Sodium on a Rectal Polyp

Observation under a dim field raises up the danger of perforation, etc. We, therefore, firstly performed fluorescence electronic endoscopy by fluorescein sodium on a polyp of a rectum where scope control is easy. An electronic endoscope (Olympus, GIF, XQ200) with a barrier filter (Kodak Wratten Filter No 15) attached to the objective lens was inserted into the rectum. After the polyp was found, one shot of fluorescein sodium, 5 ml, was intravenously injected within 2-3 seconds through a plastic catheter inserted in an antecubital vein and then the an adjuster filter (LBB (light balancing, blue) 200, Olympus) was inserted in front of the light source. In the last half of the observation, an exciter filter (Kodak Wratten Filter No 47A, a recommended filter for activating fluorescein) was put in front of the light source instead of an adjuster filter for comparison. The same lesion was also observed by white light endoscopy with another electronic endoscope. Findings were recorded by video tape, color films and video color printer.

Result

Experiment II

Fluorescence Electronic Endoscopy by Fluorescein Sodium on a Rectal Polyp

Figure 2:
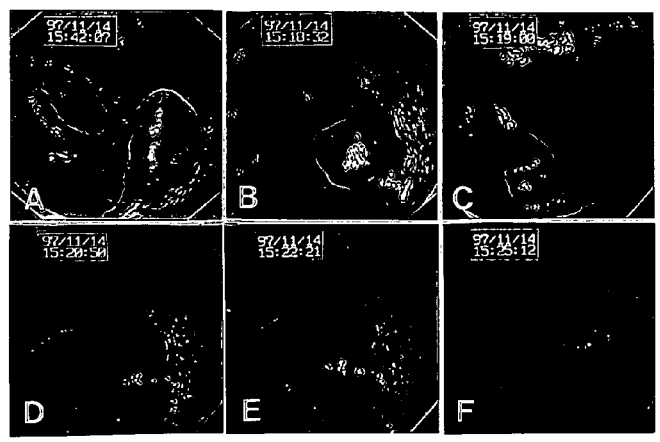
FIG. 2. Endoscopic photographs of a rectal polyp. A: routine white light endoscopy. B-E: fluorescein electronic endoscopic photographs taken in a series by inserting an adjuster filter in front of a light source in addition to an RGB band pass filters and observing by a black and white CCD with a barrier filter. F: fluorescein electronic endoscopic photograph taken by inserting an exciter filter instead of an adjuster filter.

Observed by white light endoscopy, the polyp and rectal wall looked reddish (FIG. 2A). With the barrier filter on the objective lens, the rectal wall looked yellow (FIG. 2B). After injection of fluorescein sodium and insertion of the adjuster filter in front of the light source, white fluorescence first appeared on the polyp several seconds later (FIG. 2C). In about 30 seconds or more, fluorescence appeared diffusely everywhere on the colonic wall (FIG. 2D). Fluorescence gradually faded but still could be observed for over ten minutes. The images of FEE is dimmer compared to routine observation but bright enough that one could see the details of the rectal wall (FIG. 2E). When an exciter filter was set instead of an adjuster filter, the images became dark blue and the details of rectal walls could no longer be observed (FIG. 2F). Fluorescence could still be seen when we switched back from the exciter filter to the adjuster filter.

Discussion

It has been considered up to now that fluorescence electronic endoscopy by fluorescein sodium is impossible because an FITC-interference filter, the recommended exciter filter for fluorescein fundoscopy and fluorescein fiber-endoscopy, gives very dim images when used with an electronic endoscope. An FITC-interference filter is designed to selectively pass only the desired wavelengths (450-500 nm, blue light) in order to get sharp images of fine blood vessels. In Experiment II, we have confirmed that the Kodak Wratten Filter No 47A, which passes nearly as narrow a band of blue light as the FITC-interference filter, gave so dim images that endoscope control was impossible (FIG. 2F). However, with an adjuster filter passing lot of blue light and to some extent green and red light, we were able to observe real time changes of fluorescent images bright enough to perform biopsy and to record findings under routine condition (FIGS. 2A-E).

As being declared in some congresses, there are two patterns of fluorescein electronic endoscopy on early gastric cancers. First, the lesions show no fluorescence from the beginning. Second, at first the lesions show as strong a fluorescent intensity as the surrounding tissue, but a few minutes later as fluorescence of the surrounding tissue fades away, the lesions still show strong fluorescence. In any pattern, the border line between cancers and surrounding normal tissue becomes clear. Although the pictures were not shown, if the adjuster filter is removed from the light way during the observation of fluorescein electronic endoscopy, the image becomes as bright as routine white light endoscopy, but the border lines between cancers and normal tissue become unclear. As was described in experiment I, fluorescence of fluorescein sodium can be observed without an adjuster filter because primary blue light from the light source functions as excitation light. However, by using the adjuster filter, the fluorescent intensity is emphasized and the brightness of the background image is cut down, thus the fluorescent image can be clearly observed on the background image.

The problem that the fluorescent image is usually dim can be solved by the FEES shown in FIG. 4. However, this system still has some inconvenient points. That is, with a barrier filter attached to the objective lens, it is impossible to do routine white light endoscopy and fluorescence endoscopy with the same electronic endoscope. To do both types of endoscopies, one needs to insert two different electronic endoscopes for two times. This means two times lost and double pain to patients. A way to solve this problem is using a fiberscope connected with a CCD outside the body, so that the barrier filter can be inserted in front of, or taken away from, the CCD outside the body. Another way is to contrive another new FEES.

Figure 6:
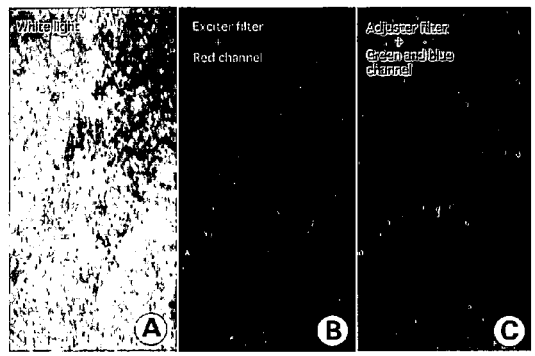
FIG. 6. Photographs of a fluorescein stain of a white paper taken by a color CCD attached to a light microscope under white light by all three channels (A), under excitation blue light by only red channels, and under light adjusted by an adjuster filter (B), which passes lot of blue light and to some portion green and red light, by blue and green channel (C).

Theoretically, it is possible to shut off exciting blue light and selectively pick up only yellow fluorescence of fluorescein sodium without a barrier filter by the use of a color CCD camera. The red channel of the color CCD camera does not react to blue light at all, but sensitively reacts to yellow fluorescence of fluorescein sodium (FIGS. 6A, B and C). Usually, it is not necessary to set up and rotate the RGB band pass filter in front of the light source in case a color CCD is used because RGB receptors on the CCD camera can react at the same time with red, green and blue components in white light, respectively.

Figure 7:
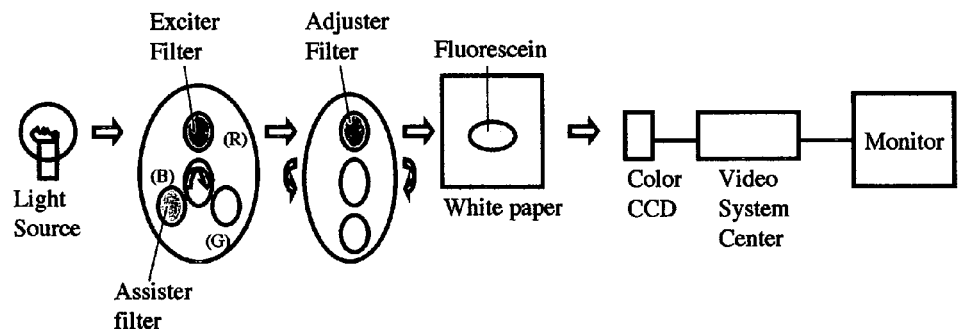
FIG. 7. Schema illustrates a fluorescence electronic endoscopic system without disposing a barrier filter before a color CCD.

An electronic endoscopic system which can perform both white light endoscopy and fluorescein electronic endoscopy would be composed of a white light source, the first frame containing a primary B filter and two pass-through holes, the second frame an adjuster filter, a color CCD behind the objective lens, and a video center system such as Olympus, CV-200 which can reconstruct electronic signals of R, G and B channels of little time lag on a TV monitor (FIG. 7). As in experiment I, suppose white paper with fluorescein stains was used as an object. White light endoscopy can be performed without rotating the first frame, which is fixed at the place where light passes through the hole with no filter, and without setting the adjuster filter in front of the light source. Fluorescein electronic endoscopy can be performed by rotating the first frame and setting the adjuster filter in front of the light source.

Figure 8:
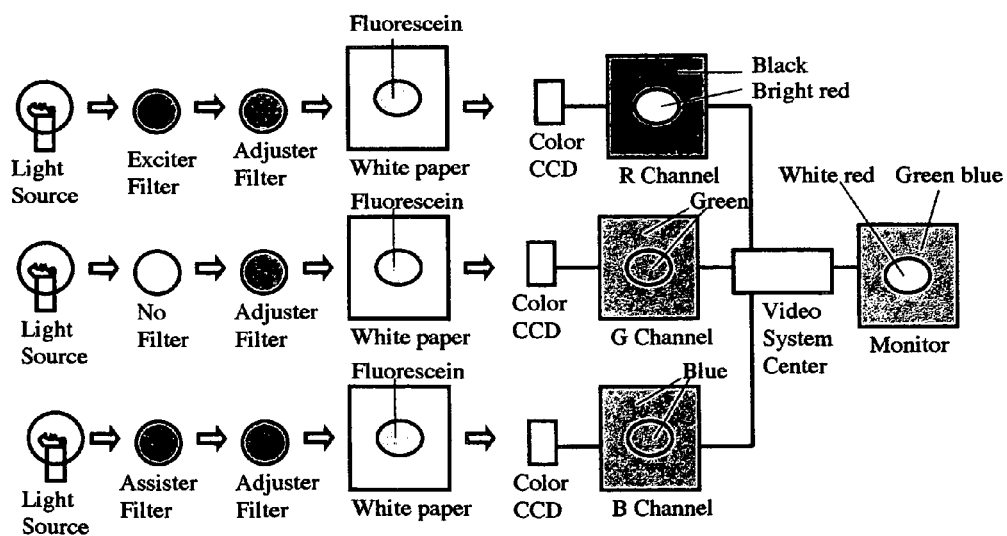
FIG. 8. Schema illustrates the mechanism of a fluorescence electronic endoscopic system without disposing a barrier filter before a color CCD.

The video center system is set up so that the R channel functions at the time the primary blue filter, which acts as an excitation filter, comes in front of the light source. B and G channels function at the time when the pass-through holes come in front of the light source, respectively. Under this condition, at the phase of R channel, exciting light having passed through the primary blue filter and the adjuster filter, activates fluorescein stain to release yellow fluorescence. Excitation blue light reflecting from the white paper does not react with the R receptor of the color CCD camera. Only yellow fluorescence is picked up as a red signal (FIG. 8). That is, the fluorescent image is picked up as a red signal by the R channel. At B and G phases, having passed through only the blue light balancing filter (adjuster filter), light consisting of a large amount of blue and small amountsof green and red light is radiating to the white paper and the fluorescein stain and the reflecting light is picked up by the G channel. This means that the B and G channels pick up the background image by light adjusted by the adjuster filter (FIG. 8). The fluorescent image and the background image are, then, coalesced on the TV monitor by the video center system. Now, the mechanism and effects of my invention titled "Method for superimposing fluorescent image on background image by CCD and viewing the images on the same screen simultaneously" have been described by using fluorescein electronic endoscopy as an example. Theoretically, the FEES described in this invention can also used for other fluorescence endoscopy, such as auto-fluorescence endoscopy and photodynamic therapy. The effects of my invention are not limited only to the electronic endoscope with a CCD at its tip. My invention can also be applied to the method in which a fiberscope is used to transmit the image and then is connected with a CCD outside the body. Not only the light source (Olympus, CLV-U20D), the electronic endoscope (Olympus, GIF, XQ 200), and the video center system (Olympus, CV-20) used in the experiments described above can give the effect of my invention.

EFFECTS OF THE INVENTION

Generally, fluorescent examination is performed by using an exciter filter, which selectively passes only the excitation light, together with a barrier filter, which cuts off all excitation light and passes through all the emitted fluorescence, to receive only the fluorescent image. There is no problem to observe fluorescent images on dark backgrounds outside the body as in fluorescein fundography. However, for endoscopy, observation under a dim field raises up the danger of perforation, etc. Moreover, it is difficult to tell from where the fluorescence is emitted with the fluorescent image only.

In a FEES of this invention, excitation light (for example, blue light) and light adjusted by an adjuster filter are alternately projected to an object under observation, the fluorescence light (for example, yellow light) is received by one channel (for example, a blue channel) out of three channels by disposing before a black-and-white CCD a barrier filter which cuts all excitation light but passes all other light, the light adjusted by an adjuster filter is received by the other two channels (for example, green and red channels) to capture the background image, the signals sent through the three channels are combined, and the fluorescent image is superimposed on the background image on a monitor. Thus, a sharp fluorescent image of bright field of view is formed and viewed on the same screen simultaneously, and the portions where fluorescence is emitted can be easily specified in the background.

The adjuster filter, which passes a lot of excitation light and to some extent other light, functions to emphasize fluorescent intensity and to cut down brightness of the background image, so that the fluorescent image is clearly seen being superimposed on the background image. In fluorescein electronic endoscopy, the adjuster filter is a blue light balancing filter which passes lot of blue light and little of green and red light.

My invention also includes a fluorescence electronic endoscopic system able to perform fluorescence endoscopy without disposing a barrier filter before a CCD, in which excitation light (for example, blue light) and light adjusted by an adjuster are alternately projected to an object under observation, the fluorescence light (for example, yellow light) is received by a channel of a color CCD (for example, red channel) which does not react with the excitation light but with the fluorescent light, the light adjusted by an adjuster and assister filter is received by the other two channels (for example, green and red channels) to capture the background image, the signals sent through the three channels are combined, and the fluorescent image is superimposed on the background image on a monitor. Thus, a sharp fluorescent image of bright field of view is formed and viewed on the same screen simultaneously, and the portions where fluorescence is emitted can be easily specified in the background. Because there is no barrier in front of the CCD, routine white light endoscopy and fluorescence endoscopy can be performed by the same electronic endoscope with only one insertion.

Fluorescence endoscopic systems on a commercial base are performed with the combination of fiberscopes and high-sensitive cameras, and need special instruments. Therefore, they are very expensive and clumsy to be operated. Another problem is that, with only a fluorescent image, one cannot observed the background clearly; thus, it is not easy to recognize which part of the tissue shows strong fluorescence when switching to white light endoscopic images. These problems can be solved by the FEES of my invention which are composed of only instruments used in routine endoscopy, and thus are smart and not expensive. Applying my invention to auto-fluorescence endoscopy and photodynamic therapy/diagnosis will help to save a lot of money.

What is claimed is:

1. A fluorescence electronic endoscopic system for viewing matter comprising, in combination:
   I) at least one excitation light emitting system structured and arranged to illuminate the subject matter with excitation light;
   II) at least one non-excitation light emitting system structured and arranged to illuminate the subject matter with non-excitation light;
   III) at least one alternating system structured and arranged to alternate use of said at least one excitation light emitting system and said at least one non-excitation light emitting system,
      ① wherein said at least one alternating system is structured and arranged to illuminate the subject matter for first periods of time essentially only said at least one excitation light emitting system, and ② wherein said at least one alternating system is structured and arranged to illuminate the subject matter for second periods of time by said at least one non-excitation light emitting system;

IV) at least image sensing system, structured and arranged to sense images of the subject matter, comprising,
① at least one color CCD inside an endoscope,
② at least three video channels, wherein:
1. at least one of said video channels, which is sensitive to the fluorescence emitted from the subject matter but not to the excitation light, is structured and arranged to differentiate without using any filters or dichroic mirrors between the excitation light and the fluorescence, and transmit only the fluorescence image during such first period of time, and
2. at least two of said video channels are structured and arranged each to transmit at least one such image sensed during such second period of time V) at least one superimposing system structured and arranged to superimpose such images sensed by said image sensing system,
① wherein at least one such image sensed during such first period of time is superimposed with at least one such image sensed during such second period of time to create at least one such superimposed image; and VI) at least one image viewing system structured and arranged to permit viewing such at least one superimposed image.

2. A fluorescence electronic endoscopic system for viewing matter comprising, in combination:

I) at least one light source for illuminating the subject matter, said at least one light source emitting light having plurality of wavelength ranges, said light comprising visible light and an excitation light;

II) at least one filter unit, arranged between said at least one light source and the subject matter, that periodically filters said light from said at least one light source to illuminate the subject matter, said at least one filter unit comprising at least one blue filter, with or without at least one red filter, and with or without at least one green filter, such that the light filtered by said at least one blue filter functions as at least one excitation light that causes the subject matter to fluoresce and emit fluorescent light, while the light unfiltered and/or the light filtered by said at least one green filter and/or the light filtered by said at least one red filter function as at least one non-excitation light;

III) at least one fluorescence filter, said at least one fluorescence filter preventing transmission of said at least one excitation light reflected from the subject matter but not of the fluorescent light emitted from the subject matter and said at least one non-excitation light reflected from the subject matter;

IV) at least one image sensing system, structured and arranged to sense images of the subject matter passing through said at least one fluorescence filter, said at least one image sensing system comprising,
① at least one black-and-white CCD provided inside an endoscope,
② at least two video channels, wherein:
1. at least one of said video channels is structured and arranged to transmit the fluorescence image sensed during the period(s) of the excitation light (s), and
2. at least one of said video channels is structured and arranged to transmit at least one such image sensed during the period(s) of the non-excitation light(s);

V) at least one superimposing system structured and arranged to superimpose such images sensed by said image sensing system,
① wherein fluorescence image sensed during the period(s) of the excitation light(s) is superimposed with at least one such image sensed during the period(s) of the non-excitation light(s) to create one such superimposed image; and VI) at least one image viewing system structured and arranged to permit viewing such at least one superimposed color image.

3. The fluorescence electronic endoscopic system according to claim 2, wherein said at least one filter unit is a rotating disk upon which said at least one blue, at least one green and at least one red filters are mounted.

4. The fluorescence electronic endoscopic system according to claim 2, wherein said at least one filter unit is a rotating disk upon which said at least one blue and at least one green filters are mounted.

5. The fluorescence electronic endoscopic system according to claim 2, wherein said at least one filter unit is a rotating disk upon which said at least one blue and at least one red filters are mounted.

6. The fluorescence electronic endoscopic system according to claim 2, wherein said at least one filter unit is a rotating disk upon which said at least one blue filter is mounted, and in which there is at least one pass-through hole.

7. The fluorescence electronic endoscopic system according to claim 2 further comprising at least one adjuster filter, said at least one adjuster filter decreasing only some of the excitation light intensity but most of the non-excitation light intensity from said at least one light source for illuminating the subject matter.

* * * * *